United States Patent
Maione et al.

(10) Patent No.: US 12,146,002 B2
(45) Date of Patent: Nov. 19, 2024

(54) POLYMER AGONISTS OF MU OPIOID RECEPTORS

(71) Applicant: CYTOGEL PHARMA, LLC, Darien, CT (US)

(72) Inventors: Theodore E. Maione, Green Island, NY (US); James Hamsher, Darien, CT (US); Constantine Basil Maglaris, Darien, CT (US)

(73) Assignee: CYTOGEL PHARMA, LLC, Darien, CT (US)

( * ) Notice: Subject to any disclaimer, the term of this patent is extended or adjusted under 35 U.S.C. 154(b) by 0 days.

(21) Appl. No.: 17/724,913

(22) Filed: Apr. 20, 2022

(65) Prior Publication Data

US 2022/0251139 A1      Aug. 11, 2022

Related U.S. Application Data

(63) Continuation of application No. 16/609,840, filed as application No. PCT/US2018/061821 on Nov. 19, 2018.

(60) Provisional application No. 62/588,013, filed on Nov. 17, 2017.

(51) Int. Cl.
| | | |
|---|---|---|
| *C07K 7/06* | (2006.01) | |
| *A61K 38/00* | (2006.01) | |
| *A61K 47/54* | (2017.01) | |
| *A61K 47/60* | (2017.01) | |
| *A61K 47/61* | (2017.01) | |
| *A61K 47/62* | (2017.01) | |
| *C07K 5/107* | (2006.01) | |

(52) U.S. Cl.
CPC ............ *C07K 7/06* (2013.01); *A61K 47/542* (2017.08); *A61K 47/60* (2017.08); *A61K 47/61* (2017.08); *A61K 47/62* (2017.08); *C07K 5/1016* (2013.01); *A61K 38/00* (2013.01)

(58) Field of Classification Search
None
See application file for complete search history.

(56) References Cited

U.S. PATENT DOCUMENTS

| | | |
|---|---|---|
| 4,277,394 A | 7/1981 | Fujino et al. |
| 4,459,225 A | 7/1984 | Teetz et al. |
| 4,559,157 A | 12/1985 | Smith et al. |
| 4,608,392 A | 8/1986 | Jacquet et al. |
| 4,820,508 A | 4/1989 | Wortzman |
| 4,938,949 A | 7/1990 | Borch et al. |
| 4,992,478 A | 2/1991 | Geria |
| 5,885,958 A | 3/1999 | Zadina et al. |
| 6,303,578 B1 | 10/2001 | Zadina et al. |
| 8,716,436 B2 | 5/2014 | Zadina et al. |
| 8,940,704 B2 | 1/2015 | Maione |
| 2009/0191579 A1 | 7/2009 | Wang et al. |
| 2011/0065648 A1 | 3/2011 | Maione |
| 2011/0190214 A1 | 8/2011 | Maione |
| 2011/0287040 A1 | 11/2011 | Maione et al. |
| 2013/0178427 A1 | 7/2013 | Zadina et al. |
| 2015/0126455 A1* | 5/2015 | Maione ................ C07K 5/1016 514/17.5 |
| 2018/0371017 A1 | 12/2018 | Maione et al. |

FOREIGN PATENT DOCUMENTS

| | | |
|---|---|---|
| EP | 0024664 A1 | 3/1981 |
| EP | 2546268 A1 | 1/2019 |
| FR | 2347336 A1 | 11/1977 |
| JP | H07503485 A | 4/1995 |
| JP | 2001505872 A | 5/2001 |
| JP | 2013530147 A | 7/2013 |
| JP | 2013533890 A | 8/2013 |
| JP | 2014531398 A | 11/2014 |
| WO | 9411018 A1 | 5/1994 |
| WO | 1998011126 A1 | 3/1998 |
| WO | 2012006497 A2 | 1/2012 |
| WO | 2013008123 A1 | 1/2013 |
| WO | 2014081864 A1 | 5/2014 |

OTHER PUBLICATIONS

Perlikowska et al. (Basic & Clinical Pharmacology & Toxicology, 106, 106-113, 2009) (Year: 2009).*
Mizoguchi, H., et al. "Involvement of spinal μ1-opioid receptors on the Tyr-d-Arg-Phe-sarcosine-induced antinociception." European journal of pharmacology 540.1-3 (2006): 67-72.
Lam, K. S., et al., "The Chemical Synthesis of Large Random Peptide Libraries and Their Use for the Discovery of Ligands for Macromolecular Acceptors." Bioorganic & Medicinal Chemistry Letters, 1993, 3(3): 419-424.
Mahajan, A., et al., "Structural Modification of Proteins and Peptides." Indian Journal of Pharmaceutical Education and Research, 2014, 48(3): 34-47.
Perlikowska, R., et al., "Pharmacological Characterization of Endomorphin-2-Based Cyclic Pentapeptides with Methylated Phenylalanine Residue." Peptides, 2014, 55: 145-150.
Piekielna, J., et al., "Cyclic Pentapeptide Analogs Based on Endomorphin-2 Structure: Cyclization Studies Using Liquid Chromatography Combined with on-line Mass Spectrometry and Tandem Mass Spectrometry." Peptides, 2014, 55: 32-40.
Piekielna, J., et al., "Ring Size in Cyclic Endomorphin-2 Analogs Modulates Receptor Binding Affinity and Selectivity." Organic & Biomolecular Chemistry, 2015, 13: 6039-6046.
Ronai, A. Z., et al., "A Novel Opioid Structure Which Accepts Protonated as well as Non-Protonated Nitrogen: A Family of Pure, Delta Receptor Selective Antagonists." Life Sciences, 1992, 50(18): 1371-1378.

(Continued)

*Primary Examiner* — Sergio Coffa
(74) *Attorney, Agent, or Firm* — SALIWANCHIK, LLOYD & EISENSCHENK

(57) ABSTRACT

The subject invention provides compositions and methods for alleviating pain. Specifically, the subject invention provides pharmaceutical formulations of polymers, and/or their salts, having advantageous μ-opioid receptor binding activity.

13 Claims, 1 Drawing Sheet
Specification includes a Sequence Listing.

(56) References Cited

OTHER PUBLICATIONS

Schiller, P. W. et al. "A novel side-chain-linked antiparallel cyclic dimer of enkephalin." FEBS letters 191.2 (1985):231-234.
Shinagawa, S., et al., "Synthetic Studies on Enkephalin Analogs. III. A Highly Potent Enkephalin Analog, H-Tyr-D-Met(O)-Gly-Phe-NHNH-CO-CH2CH3." Chemical and Pharmaceutical Bulletin, 1981, 29(12): 3646-3659.
Wang, W., et al., "A Tetra-Layer Microfluidic System for Peptide Affinity Screening Through Integrated Sample Injection." Analyst, 2013, 138(10): 2890-2896.

* cited by examiner

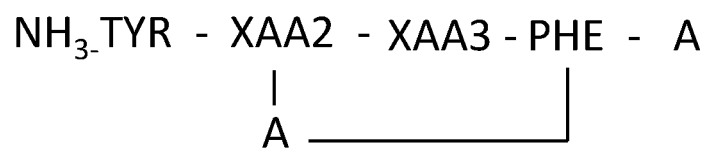
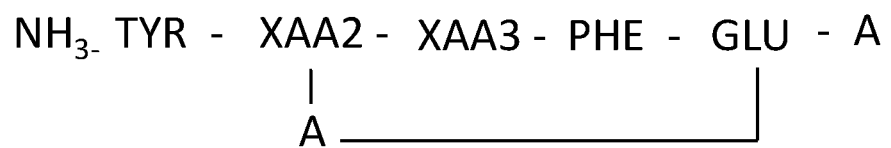
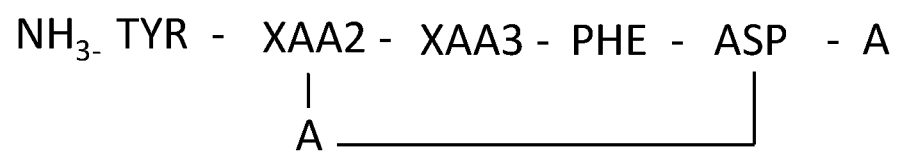

POLYMER AGONISTS OF MU OPIOID RECEPTORS

CROSS REFERENCE TO A RELATED APPLICATION

This application is a continuation of U.S. patent application Ser. No. 16/609,840, filed Oct. 31, 2019; which is a National Stage Application of International Application No. PCT/US2018/061821, filed Nov. 19, 2018; which claims the benefit of U.S. Provisional Application Ser. No. 62/588,013, filed Nov. 17, 2017, all of which are hereby incorporated by reference in their entirety.

SEQUENCE LISTING

The Sequence Listing for this application is labeled "SeqList-16May23_ST25.txt," which was created May 16, 2023, and is 4-17 KB. The Sequence Listing is incorporated herein by reference in its entirety.

BACKGROUND OF THE INVENTION

The major function for opiates is their role in alleviating pain. Other areas where opiates are well-suited for use are conditions relating to gastrointestinal disorders, schizophrenia, obesity, blood pressure, convulsions, and seizures.

Three different opiate receptors have been found: delta ($\delta$), kappa ($\kappa$) and mu ($\mu$). Endomorphin-1 peptide (EM-1) and its analogs have been found to exhibit opiate-like activity by binding to the $\mu$ opiate receptor.

Activation of the $\mu$ receptor is among the most effective means of alleviating a wide range of pain conditions. The unique effectiveness of $\mu$ agonists can be attributed to several factors, including their presence in numerous regions of the nervous system that regulate pain processing and activation of multiple mechanisms that limit pain transmission (e.g., inhibiting release of excitatory transmitters from the peripheral nervous system and decreasing cellular excitability in the central nervous system).

Limitations on the use of opioids result from negative side effects, including abuse liability, respiratory depression, and cognitive and motor impairment. Major efforts to develop compounds that maintain analgesic properties while reducing the negative side effects have met with limited success. This is evident from the current epidemic of prescription drug abuse.

Natural endogenous peptides from bovine and human brain that are highly selective for the $\mu$ opioid receptor relative to the delta or kappa receptor have been described (see, for example, U.S. Pat. No. 6,303,578 which is incorporated herein by reference in its entirety). These peptides are potent analgesics and have shown promise of reduced abuse liability and respiratory depression.

Cyclized, D-amino acid-containing tetrapeptide analogs of the endomorphins (U.S. Pat. No. 5,885,958 which is incorporated herein by reference in its entirety) have also been described.

Annually, over 100 million patients in the United States experience acute or chronic pain and frequently do not achieve adequate relief from existing drugs due to limited efficacy and/or excessive side effects. Therefore, agonists of opioid receptors having improved solubility and other properties are desirable.

BRIEF SUMMARY OF THE INVENTION

The subject invention provides polymers, modified polymers, and/or their salts, having advantageous $\mu$-opioid receptor agonist activity. The polymers can be linear or cyclic and comprise or consist of between 4 to 6 residues, one or more of which can, optionally, be conjugated to one or more moieties.

In certain embodiments, linear polymers of the invention comprise or consist of four, five, or six residues. In some embodiments, a linear polymer comprises or consists of SEQ ID NO: 1: $\text{Tyr}^1\text{-Xaa}^2\text{-Xaa}^3\text{-Phe}^4$, with the proviso that: either $\text{Xaa}^2$ is a residue other than lysine, glutamate, aspartate, ornithine, or proline; or $\text{Xaa}^3$ is a residue other than an aromatic amino acid.

For example, $\text{Xaa}^2$ can be arginine, D-2-amino-3-guanidinopropionic acid, GABA, citrulline, tranexamic acid, aminocaproic acid, serine, threonine, glutamine, asparagine, histidine, 4-oxaproline, 4-thioproline, 2-azaproline, 4-hydroxyproline, 1,5-disubstituted tetrazole, 2-amino isobutyric acid, sarcosine, 1-aminocyclopentane-1-carboxylic acid, beta alanine, 2-amino-cyclopentane carboxylic acid (beta-proline), 5-hydroxylysine, hydroxylysine-5-sulfate, hydroxylysine-5-nitrate, hydroxylysine-5-phosphate, serine-3-sulfate, threonine-3-sulfate, serine-3-nitrate, threonine-3-nitrate, serine-3-phosphate, threonine-3-phosphate, or 2-hydroxy alkanoic acid, and $\text{Xaa}^3$ can be an amino acid.

Alternatively, $\text{Xaa}^2$ can be lysine, glutamate, aspartate, ornithine, arginine, D-2-amino-3-guanidinopropionic acid, gamma-amino butyric acid (GABA), citrulline, tranexamic acid, aminocaproic acid, proline, serine, threonine, glutamine, asparagine, histidine, 4-oxaproline, 4-thioproline, 2-azaproline, 4-hydroxyproline, 1,5-disubstituted tetrazole, 2-amino isobutyric acid, sarcosine, 1-aminocyclopentane-1-carboxylic acid, beta alanine, 2-amino-cyclopentane carboxylic acid (beta-proline), 5-hydroxylysine, hydroxylysine-5-sulfate, hydroxylysine-5-nitrate, hydroxylysine-5-phosphate, serine-3-sulfate, threonine-3-sulfate, serine-3-nitrate, threonine-3-nitrate, serine-3-phosphate, threonine-3-phosphate, or 2-hydroxy alkanoic acid, and $\text{Xaa}^3$ is a residue other than an aromatic amino acid In preferred embodiments, the $\text{Xaa}^2$ is lysine, glutamate, aspartate, ornithine, arginine, D-2-amino-3-guanidinopropionic acid, gamma-amino butyric acid (GABA), citrulline, tranexamic acid, aminocaproic acid, proline, serine, threonine, glutamine, asparagine, histidine, 4-oxaproline, 4-thioproline, 2-azaproline, 4-hydroxyproline, 1,5-disubstituted tetrazole, 2-amino isobutyric acid, sarcosine, 1-aminocyclopentane-1-carboxylic acid, beta alanine, 2-amino-cyclopentane carboxylic acid (beta-proline), 5-hydroxylysine, hydroxylysine-5-sulfate, hydroxylysine-5-nitrate, hydroxylysine-5-phosphate, serine-3-sulfate, threonine-3-sulfate, serine-3-nitrate, threonine-3-nitrate, serine-3-phosphate, or threonine-3-phosphate. In preferred embodiments, the $\text{Xaa}^2$ is in the D-configuration.

In further embodiments, $\text{Xaa}^2$ is a hydroxy alkanoic acid, particularly, 2-hydroxy alkanoic acid, that can form ester linkages with $\text{Tyr}^1$ and that can also optionally form ester linkages with other residues of the polymer to produce cyclic polymers. In certain embodiments, $\text{Xaa}^3$ is phenylalanine or tryptophan.

In preferred embodiments, a linear polymer of the invention comprising or consisting of the sequence of SEQ ID NO: 1 is modified by conjugation at: the $X^2$ position to a moiety selected from $NH_2$, an amino acid, a peptide, polyethylene glycol (PEG), polysaccharide, a free carboxyl group, an amidated carboxyl group, or a fatty acid and/or the $X^4$ position to a moiety selected from $NH_2$, an amino acid, a peptide, PEG, polysaccharide, a free carboxyl group, an amidated carboxyl group, or a fatty acid.

In further embodiments of the subject invention, the polymer comprises or consists of SEQ ID NO: 2: Tyr$^1$-Xaa$^2$-Xaa$^3$-Phe$^4$-Glu$^5$ or SEQ ID NO: 3: Tyr$^1$-Xaa$^2$-Xaa$^3$-Phe$^4$-Asp$^5$, with the proviso that: either Xaa$^2$ is a residue other than lysine, glutamate, aspartate, ornithine, or proline; or Xaa$^3$ is a residue other than an aromatic amino acid.

For example, Xaa$^2$ can be arginine, D-2-amino-3-guanidinopropionic acid, GABA, citrulline, tranexamic acid, aminocaproic acid, serine, threonine, glutamine, asparagine, histidine, 4-oxaproline, 4-thioproline, 2-azaproline, 4-hydroxyproline, 1,5-disubstituted tetrazole, 2-amino isobutyric acid, sarcosine, 1-aminocyclopentane-1-carboxylic acid, beta alanine, 2-amino-cyclopentane carboxylic acid (beta-proline), 5-hydroxylysine, hydroxylysine-5-sulfate, hydroxylysine-5-nitrate, hydroxylysine-5-phosphate, serine-3-sulfate, threonine-3-sulfate, serine-3-nitrate, threonine-3-nitrate, serine-3-phosphate, threonine-3-phosphate, or 2-hydroxy alkanoic acid, and Xaa$^3$ can be an amino acid.

Alternatively, Xaa$^2$ can be lysine, glutamate, aspartate, ornithine, arginine, D-2-amino-3-guanidinopropionic acid, gamma-amino butyric acid (GABA), citrulline, tranexamic acid, aminocaproic acid, proline, serine, threonine, glutamine, asparagine, histidine, 4-oxaproline, 4-thioproline, 2-azaproline, 4-hydroxyproline, 1,5-disubstituted tetrazole, 2-amino isobutyric acid, sarcosine, 1-aminocyclopentane-1-carboxylic acid, beta alanine, 2-amino-cyclopentane carboxylic acid (beta-proline), 5-hydroxylysine, hydroxylysine-5-sulfate, hydroxylysine-5-nitrate, hydroxylysine-5-phosphate, serine-3-sulfate, threonine-3-sulfate, serine-3-nitrate, threonine-3-nitrate, serine-3-phosphate, threonine-3-phosphate, or 2-hydroxy alkanoic acid, and Xaa$^3$ is a residue other than an aromatic amino acid In some embodiments, Xaa$^2$ in SEQ ID NO: 2 or 3 is lysine, glutamate, aspartate, ornithine, arginine, D-2-amino-3-guanidinopropionic acid, GABA, citrulline, tranexamic acid, aminocaproic acid, proline, serine, threonine, glutamine, asparagine, histidine, 4-oxaproline, 4-thioproline, 2-azaproline, 4-hydroxyproline, 1,5-disubstituted tetrazole, 2-amino isobutyric acid, sarcosine, 1-aminocyclopentane-1-carboxylic acid, beta alanine, 2-amino-cyclopentane carboxylic acid (beta-proline), 5-hydroxylysine, hydroxylysine-5-sulfate, hydroxylysine-5-nitrate, hydroxylysine-5-phosphate, serine-3-sulfate, threonine-3-sulfate, serine-3-nitrate, threonine-3-nitrate, serine-3-phosphate, or threonine-3-phosphate. In more preferred embodiments, the Xaa$^2$ is in D-configuration.

In further embodiments, Xaa$^2$ is a hydroxy alkanoic acid, particularly, 2-hydroxy alkanoic acid that can form ester linkages with Tyr$^1$ and that can also optionally for ester linkages with other residues of the polymer to produce cyclic polymers. In certain embodiments, Xaa$^3$ is phenylalanine or tryptophan.

In particular embodiments, a linear polymer of the invention comprising or consisting of the sequence of SEQ ID NO: 2 or 3 is modified by conjugating at: the X$^2$ position to a moiety selected from NH$_2$, an amino acid, a peptide, PEG, polysaccharide, a free carboxyl group, an amidated carboxyl group, or a fatty acid and/or the X$^5$ position to a moiety selected from NH$_2$, an amino acid, a peptide, PEG, polysaccharide, a free carboxyl group, an amidated carboxyl group, or a fatty acid.

In some embodiments, the polymer comprises or consists of SEQ ID NO: 4: Tyr$^1$-c[Xaa$^2$-Xaa$^3$-Phe$^4$-Glu$^5$] or SEQ ID NO: 5: Tyr$^1$-c[Xaa$^2$-Xaa$^3$-Phe$^4$-Asp$^5$]. Xaa$^2$ can be lysine, glutamate, aspartate, ornithine, arginine, D-2-amino-3-guanidinopropionic acid, GABA, citrulline, tranexamic acid, aminocaproic acid, proline, serine, threonine, glutamine, asparagine, histidine, 4-oxaproline, 4-thioproline, 2-azaproline, 4-hydroxyproline, 1,5-disubstituted tetrazole, 2-amino isobutyric acid, sarcosine, 1-aminocyclopentane-1-carboxylic acid, beta alanine, 2-amino-cyclopentane carboxylic acid (beta-proline), 5-hydroxylysine, hydroxylysine-5-sulfate, hydroxylysine-5-nitrate, hydroxylysine-5-phosphate, serine-3-sulfate, threonine-3-sulfate, serine-3-nitrate, threonine-3-nitrate, serine-3-phosphate, or threonine-3-phosphate.

In further embodiments, Xaa$^2$ is a hydroxy alkanoic acid, particularly, 2-hydroxy alkanoic acid that can form ester linkages with Tyr$^1$ and that can also optionally for ester linkages with other residues of the polymer to produce cyclic polymers. In certain embodiments, Xaa$^3$ is phenylalanine or tryptophan.

The polymer of SEQ ID NO: 4 or 5 can also be conjugated to a moiety selected from NH$_2$, an amino acid, a peptide, PEG, polysaccharide, a free carboxyl group, an amidated carboxyl group, or a fatty acid.

Further embodiments of the invention provide pharmaceutical compositions comprising the polymers, modified polymers, and/or their salts and pharmaceutically acceptable carriers and/or excipients. Methods of treating a disease in a subject by administering to the subject the polymers, modified polymers, and/or their salts as well as the pharmaceutical compositions thereof are also provided.

BRIEF DESCRIPTION OF DRAWINGS

FIG. 1 provides schematic representation of certain polymers of the invention and modifications thereof. "A" indicates NH$_2$, amino acid(s), peptide, PEG, polysaccharide, a free carboxyl group, an amidated carboxyl group, or a fatty acid. Also, "A" in the ring connecting XAA2 with PHE, GLU, or ASP is optional. Similarly, "A" connected to the end of the polymer is also optional. The bond between XAA2 and PHE denotes that these polymers are cyclic. The bond between XAA2 and PHE is optional and this polymer can be a linear polymer. Similarly, the bond between XAA2 and GLU as well as the bond between XAA2 and ASP denote that these polymers are cyclic. The bond between XAA2 and GLU is optional and this polymer can be a linear polymer. Similarly, the bond between XAA2 and ASP is optional and this polymer can be a linear polymer.

BRIEF DESCRIPTION OF THE SEQUENCES

SEQ ID NOs: 1 to 5 provide sequences of the polymers useful according to the subject invention.

DETAILED DESCRIPTION OF THE INVENTION

The subject invention provides compositions and methods for alleviating pain. Specifically, the subject invention provides polymers, modified polymers, and/or their salts, having advantageous µ-opioid receptor agonist activity. Advantageously, the polymers comprise or consist of 4 to 6 residues comprising amino acids and/or organic acids, one or more of which can be conjugated to one or more moieties. In preferred embodiments, the polymer is a linear polymer comprising or consisting of 4 or 5 residues comprising amino acids and/or organic acids, optionally, modified by conjugation to one or more moieties. In other embodiments, the polymers are cyclic polymers comprising or consisting of 4 or 5 amino acids and/or organic acids, optionally, modified by conjugation to one or more moieties.

Linear Polymers of the Invention

In certain embodiments, the invention provides linear polymers comprising or consisting of 4, 5, or 6 residues comprising amino acids and/or organic acids. In preferred embodiments, the polymer is a linear polymer comprising or consisting of 4 residues comprising amino acids and/or organic acids, optionally, modified by conjugation to one or more moieties.

In some embodiments, the polymer comprises or consists of SEQ ID NO: 1: $Tyr^1$-$Xaa^2$-$Xaa^3$-$Phe^4$.

A residue position in a SEQ ID NO is referenced as $X^y$ or $Xaa^y$ wherein X or Xaa represents the residue and y represents the position of the residue in the sequence. For example, $X^2$ or $Xaa^2$ in SEQ ID NO: 1 refers to $Xaa^2$ and $X^4$ or $Xaa^4$ in SEQ ID NO: 1 refers to $Phe^4$.

In certain embodiments, the polymer comprises or consists of SEQ ID NO: 1: $Tyr^1$-$Xaa^2$-$Xaa^3$-$Phe^4$, with the proviso that: either $Xaa^2$ is a residue other than lysine, glutamate, aspartate, ornithine, or proline; or $Xaa^3$ is a residue other than an aromatic amino acid.

For example, $Xaa^2$ can be arginine, D-2-amino-3-guanidinopropionic acid, GABA, citrulline, tranexamic acid, aminocaproic acid, serine, threonine, glutamine, asparagine, histidine, 4-oxaproline, 4-thioproline, 2-azaproline, 4-hydroxyproline, 1,5-disubstituted tetrazole, 2-amino isobutyric acid, sarcosine, 1-aminocyclopentane-1-carboxylic acid, beta alanine, 2-amino-cyclopentane carboxylic acid (beta-proline), 5-hydroxylysine, hydroxylysine-5-sulfate, hydroxylysine-5-nitrate, hydroxylysine-5-phosphate, serine-3-sulfate, threonine-3-sulfate, serine-3-nitrate, threonine-3-nitrate, serine-3-phosphate, threonine-3-phosphate, or 2-hydroxy alkanoic acid, and $Xaa^3$ can be an amino acid.

Alternatively, $Xaa^2$ can be lysine, glutamate, aspartate, ornithine, arginine, D-2-amino-3-guanidinopropionic acid, gamma-amino butyric acid (GABA), citrulline, tranexamic acid, aminocaproic acid, proline, serine, threonine, glutamine, asparagine, histidine, 4-oxaproline, 4-thioproline, 2-azaproline, 4-hydroxyproline, 1,5-disubstituted tetrazole, 2-amino isobutyric acid, sarcosine, 1-aminocyclopentane-1-carboxylic acid, beta alanine, 2-amino-cyclopentane carboxylic acid (beta-proline), 5-hydroxylysine, hydroxylysine-5-sulfate, hydroxylysine-5-nitrate, hydroxylysine-5-phosphate, serine-3-sulfate, threonine-3-sulfate, serine-3-nitrate, threonine-3-nitrate, serine-3-phosphate, threonine-3-phosphate, or 2-hydroxy alkanoic acid, and $Xaa^3$ is a residue other than an aromatic amino acid.

In certain embodiments, the polymers disclosed herein exclude the peptides disclosed in the U.S. Pat. No. 8,716,436.

In preferred embodiments, $Xaa^2$ in SEQ ID NO: 1 is lysine, glutamate, aspartate, ornithine, arginine, D-2-amino-3-guanidinopropionic acid, GABA, citrulline, tranexamic acid, aminocaproic acid, proline, serine, threonine, glutamine, asparagine, histidine, 4-oxaproline, 4-thioproline, 2-azaproline, 4-hydroxyproline, 1,5-disubstituted tetrazole, 2-amino isobutyric acid, sarcosine, 1-aminocyclopentane-1-carboxylic acid, beta alanine, 2-amino-cyclopentane carboxylic acid (beta-proline), 5-hydroxylysine, hydroxylysine-5-sulfate, hydroxylysine-5-nitrate, hydroxylysine-5-phosphate, serine-3-sulfate, threonine-3-sulfate, serine-3-nitrate, threonine-3-nitrate, serine-3-phosphate, or threonine-3-phosphate. In more preferred embodiments, the $Xaa^2$ is in D-configuration.

In further embodiments, $Xaa^2$ is a hydroxy alkanoic acid, particularly, 2-hydroxy alkanoic acid. When $Xaa^2$ is a 2-hydroxy acid, $Xaa^2$ connects with $Tyr^1$ via an ester linkage. Such alkanoic acid can contain between three and twelve carbon atoms. In some embodiments, $Xaa^2$ can also have additional hydroxyl groups, preferably on the carbon atoms away from the carboxyl group towards the end of the carbon chain, for example, on any of the last three carbon atoms of the carbon chain. These hydroxyl groups can be used to form a link with the other residues of the polymers to form cyclic polymers. Non-limiting examples of such hydroxy and dihydroxy acids include 2,4-dihydroxy butanoic acid, 2,5-dihydroxypentanoic acid, 2,6-dihydroxyhexanoic acid, gluconic acid. Additional examples of hydroxy and dihydroxy acids suitable as $Xaa^2$ residue that can form ester linkages with $Tyr^1$ and that can also optionally for ester linkages with other residues of the polymer to produce cyclic polymers are known in the art and such embodiments are within the purview of the invention.

In certain embodiments, $Xaa^3$ is phenylalanine or tryptophan.

In particular embodiments, a linear polymer of the invention having the sequence of SEQ ID NO: 1 is modified by conjugating it with one or more moieties. For example, a polymer of SEQ ID NO: 1 can be modified at residue positions $X^1$, $X^2$, $X^3$, or $X^4$. In preferred embodiments, a polymer of SEQ ID NO: 1 is modified at residue positions $X^2$ and/or $X^4$.

A polymer having SEQ ID NO: 1 can be conjugated at the $X^2$ and/or $X^4$ position(s) to a moiety selected from N112, an amino acid, a peptide, PEG, polysaccharide, a free carboxyl group, an amidated carboxyl group, or a fatty acid.

In some embodiments, only one of $X^2$ and $X^4$ positions is modified by such conjugation. Also, both $X^2$ and $X^4$ positions can be modified by such conjugation. When both $X^2$ and $X^4$ positions are modified, $X^2$ and $X^4$ positions can be conjugated to identical or different moieties. In some embodiments, the $X^2$ and $X^4$ positions can be conjugated to moieties that conjugate with each other to form a ring. Any combination of moieties at the $X^2$ and $X^4$ positions are envisioned.

In further embodiments of the subject invention, the polymer is SEQ ID NO: 2: $Tyr^1$-$Xaa^2$-$Xaa^3$-$Phe^4$-$Glu^5$ or SEQ ID NO: 3: $Tyr^1$-$Xaa^2$-$Xaa^3$-$Phe^4$-$Asp^5$.

In certain embodiments, the polymer comprises or consists of SEQ ID NO: 2: $Tyr^1$-$Xaa^2$-$Xaa^3$-$Phe^4$-$Glu^5$ or SEQ ID NO: 3: $Tyr^1$-$Xaa^2$-$Xaa^3$-$Phe^4$-$Asp^5$, with the proviso that: either $Xaa^2$ is a residue other than lysine, glutamate, aspartate, ornithine, or proline; or $Xaa^3$ is a residue other than an aromatic amino acid.

For example, $Xaa^2$ can be arginine, D-2-amino-3-guanidinopropionic acid, GABA, citrulline, tranexamic acid, aminocaproic acid, serine, threonine, glutamine, asparagine, histidine, 4-oxaproline, 4-thioproline, 2-azaproline, 4-hydroxyproline, 1,5-disubstituted tetrazole, 2-amino isobutyric acid, sarcosine, 1-aminocyclopentane-1-carboxylic acid, beta alanine, 2-amino-cyclopentane carboxylic acid (beta-proline), 5-hydroxylysine, hydroxylysine-5-sulfate, hydroxylysine-5-nitrate, hydroxylysine-5-phosphate, serine-3-sulfate, threonine-3-sulfate, serine-3-nitrate, threonine-3-nitrate, serine-3-phosphate, threonine-3-phosphate, or 2-hydroxy alkanoic acid, and $Xaa^3$ can be an amino acid.

Alternatively, $Xaa^2$ can be lysine, glutamate, aspartate, ornithine, arginine, D-2-amino-3-guanidinopropionic acid, gamma-amino butyric acid (GABA), citrulline, tranexamic acid, aminocaproic acid, proline, serine, threonine, glutamine, asparagine, histidine, 4-oxaproline, 4-thioproline, 2-azaproline, 4-hydroxyproline, 1,5-disubstituted tetrazole, 2-amino isobutyric acid, sarcosine, 1-aminocyclopentane-1-carboxylic acid, beta alanine, 2-amino-cyclopentane carboxylic acid (beta-proline), 5-hydroxylysine, hydroxylysine-5- sulfate, hydroxylysine-5-nitrate, hydroxylysine-5-phosphate, serine-3-sulfate, threonine-3-sulfate, serine-3-nitrate, threonine-3-nitrate, serine-3-phosphate, threonine-3-phosphate, or 2-hydroxy alkanoic acid, and $Xaa^3$ is a residue other than an aromatic amino acid.

In certain embodiments, the polymers disclosed herein exclude the peptides disclosed in the U.S. Pat. No. 8,716,436.

In preferred embodiments, $Xaa^2$ in SEQ ID NO: 2 or 3 is lysine, glutamate, aspartate, ornithine, arginine, D-2-amino-3-guanidinopropionic acid, GABA, citrulline, tranexamic acid, aminocaproic acid, proline, serine, threonine, glutamine, asparagine, histidine, 4-oxaproline, 4-thioproline, 2-azaproline, 4-hydroxyproline, 1,5-disubstituted tetrazole, 2-amino isobutyric acid, sarcosine, 1-aminocyclopentane-1-carboxylic acid, beta alanine, 2-amino-cyclopentane carboxylic acid (beta-proline), 5-hydroxylysine, hydroxylysine-5-sulfate, hydroxylysine-5-nitrate, hydroxylysine-5-phosphate, serine-3-sulfate, threonine-3-sulfate, serine-3-nitrate, threonine-3-nitrate, serine-3-phosphate, or threonine-3-phosphate. In more preferred embodiments, the $Xaa^2$ is in D-configuration. In more preferred embodiments, the $Xaa^2$ is in D-configuration.

In further embodiments, $Xaa^2$ is a hydroxy alkanoic acid, particularly, 2-hydroxy alkanoic acid. When $Xaa^2$ is a 2-hydroxy acid, $Xaa^2$ connects with $Tyr^1$ via ester linkage. Such alkanoic acid can contain between three and twelve carbon atoms. In some embodiments, $Xaa^2$ can also have additional hydroxyl groups, preferably on the carbon atoms away from the carboxyl group towards the end of the carbon chain, for example, on any of the last three carbon atoms of the carbon chain. These hydroxyl groups can be used to form a link with the other residues of the polymers to form cyclic polymers. Non-limiting examples of such hydroxy and dihydroxy acids include 2,4-dihydroxy butanoic acid, 2,5-dihydroxypentanoic acid, 2,6-dihydroxyhexanoic acid, gluconic acid. Additional examples of hydroxy and dihydroxy acids suitable as $Xaa^2$ residue that can form ester linkages with $Tyr^1$ and that can also optionally for ester linkages with other residues of the polymer to produce cyclic polymers are known in the art and such embodiments are within the purview of the invention.

In certain embodiments, $Xaa^3$ is phenylalanine or tryptophan. In particular embodiments, a linear polymer of the invention having the sequence of SEQ ID NO: 2 or 3 is modified by conjugating to one or more moieties. For example, a polymer of SEQ ID NOs: 2 or 3 can be modified at residue positions $X^1$, $X^2$, $X^3$, $X^4$ or $X^5$. In preferred embodiments, a polymer of SEQ ID NO: 2 or 3 is modified at the residue positions $X^2$ and/or $X^5$.

A polymer having SEQ ID NO: 2 or 3 can be conjugated at the $X^2$ and/or $X^5$ position(s) to a moiety selected from $NH_2$, an amino acid, a peptide, PEG, polysaccharide, a free carboxyl group, an amidated carboxyl group, or a fatty acid. In some embodiments, only one of the $X^2$ and $X^5$ positions is modified by such conjugation. Also, both the $X^2$ and $X^5$ positions can be modified by such conjugation. When both the $X^2$ and $X^5$ positions are modified, $X^2$ and $X^5$ positions can be conjugated to identical or different moieties. In some embodiments, the $X^2$ and $X^4$ positions can be conjugated to moieties that conjugate with each other to form a ring. Any combination of moieties at the $X^2$ and $X^4$ positions are envisioned.

In some embodiments the subject invention provides salts of the linear polymers described herein. The salts can be a salt with an inorganic acid, such as hydrochloric acid, hydrobromic acid, perchloric acid, nitric acid, thiocyanic acid, sulfuric acid, and phosphoric acid; an organic acid, such as trifluoroacetic acid (TFA), formic acid, acetic acid, propionic acid, glycolic acid, lactic acid, pyruvic acid, oxalic acid, malonic acid, succinic acid, maleic acid, and fumaric acid; or a salt with a base, such as sodium hydroxide, ammonium hydroxide, potassium hydroxide, and organic bases such as mono-, di-, trialkyl and aryl amines, and substituted ethanolamines.

Further salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-di sulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent polymer either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the polymer contains a basic functionality, salts of non-toxic organic or inorganic acids, such as hydrochloride, hydrobromide, tartrate, mesylate, acetate, maleate, oxalate and the like.

Certain embodiments provide amorphous forms of salts of the linear polymers disclosed herein. Such amorphous forms are advantageous for oral, pulmonary, buccal, suppository delivery.

Cyclic Polymers of the Invention

In certain embodiments, the polymers of SEQ ID NO: 1: $Tyr^1$-$Xaa^2$-$Xaa^3$-$Phe^4$ can be cyclized. Such cyclization can be produced by forming a linkage between $Xaa^2$ and $Phe^4$, particularly, carboxyl group of $Phe^4$ and a functional group of $Xaa^2$. For example, the carboxyl group of $Phe^4$ can form an ester linkage with hydroxyl group, when present, in $Xaa^2$.

In some embodiments of the subject invention, the polymer is a cyclic polymer of SEQ ID NO: 4: $Tyr^1$-c[$Xaa^2$-$Xaa^3$-$Phe^4$-$Glu^5$] or SEQ ID NO: 5: $Tyr^1$-c[$Xaa^2$-$Xaa^3$-$Phe^4$-$Asp^5$] or a salt thereof. The salt can be a salt with an inorganic acid, such as hydrochloric acid, hydrobromic acid, perchloric acid, nitric acid, thiocyanic acid, sulfuric acid, and phosphoric acid; an organic acid, such as trifluoroacetic acid (TFA), formic acid, acetic acid, propionic acid, glycolic acid, lactic acid, pyruvic acid, oxalic acid, malonic acid, succinic acid, maleic acid, and fumaric acid; or a salt with a base, such as sodium hydroxide, ammonium hydroxide, potassium hydroxide, and organic bases such as mono-, di-, trialkyl and aryl amines, and substituted ethanolamines.

Further salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-di sulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent polymer either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the polymer contains a basic functionality, salts of non-toxic organic or inorganic acids, such as hydrochloride, hydrobromide, tartrate, mesylate, acetate, maleate, oxalate and the like.

Certain embodiments provide amorphous forms of salts of the cyclic polymers disclosed herein. Such amorphous forms are advantageous for oral, pulmonary, buccal, suppository delivery.

In preferred embodiments, $Xaa^2$ in SEQ ID NO: 4 or 5 is lysine, glutamate, aspartate, ornithine, arginine, D-2-amino-3-guanidinopropionic acid, GABA, citrulline, tranexamic acid, aminocaproic acid, proline, serine, threonine, glutamine, asparagine, histidine, 4-oxaproline, 4-thioproline, 2-azaproline, 4-hydroxyproline, 1,5-disubstituted tetrazole, 2-amino isobutyric acid, sarcosine, 1-aminocyclopentane-1-carboxylic acid, beta alanine, 2-amino-cyclopentane carboxylic acid (beta-proline), 5-hydroxylysine, hydroxylysine-5-sulfate, hydroxylysine-5-nitrate, hydroxylysine-5-phosphate, serine-3-sulfate, threonine-3-sulfate, serine-3-nitrate, threonine-3-nitrate, serine-3-phosphate, or threonine-3-phosphate. In more preferred embodiments, the $Xaa^2$ is in D-configuration. In certain embodiments, $Xaa^2$ is in D-configuration.

In further embodiments, $Xaa^2$ is a hydroxy alkanoic acid, particularly, 2-hydroxy alkanoic acid. When $Xaa^2$ is a 2-hydroxy acid, $Xaa^2$ connects with $Tyr^1$ via ester linkage. Such alkanoic acid can contain between three and twelve carbon atoms. In some embodiments, $Xaa^2$ can also have additional hydroxyl groups, preferably on the carbon atoms away from the carboxyl group towards the end of the carbon chain, for example, on any of the last three carbon atoms of the carbon chain. These hydroxyl groups can be used to form a link with the other residues of the polymers to form cyclic polymers. Non-limiting examples of such hydroxy and dihydroxy acids include 2,4-dihydroxy butanoic acid, 2,5-dihydroxypentanoic acid, 2,6-dihydroxyhexanoic acid, gluconic acid. Additional examples of hydroxy and dihydroxy acids suitable as $Xaa^2$ residue that can form ester linkages with $Tyr^1$ and that can also optionally for ester linkages with other residues of the polymer to produce cyclic polymers are known in the art and such embodiments are within the purview of the invention.

In certain embodiments, $Xaa^3$ is phenylalanine or tryptophan.

In certain embodiments, a polymer of SEQ ID NO: 4 or 5 is conjugated to a moiety selected from $NH_2$, an amino acid, a peptide, PEG, polysaccharide, a free carboxyl group, an amidated carboxyl group, or a fatty acid.

In certain embodiments, the linear polymers, the cyclic polymers, or the modified polymers disclosed herein are further conjugated to L-3,4-dihydroxyphenylalanine (L-DOPA).

Substitutions at the $X^2$ positions of polymers of SEQ ID NOs: 1 to 5 confer desirable qualities to these polymers. Such desirable qualities include resistance to protease mediated degradation, particularly, in D-configuration; increased aqueous solubility. These substitutes also provide sites for further modifications of the polymers of the invention.

In specific embodiments, the polymers described herein are not the peptides disclosed in U.S. Pat. Nos. 6,303,578, 5,885,958, or 8,716,436.

Formulations comprising any of the polymers disclosed herein are also provided. Formulations of the subject invention can contain polymers having the sequence selected from SEQ ID NO: 1 to 5, optionally, modified as discussed above.

In certain embodiments, the formulations comprise a polymer and PEG, optionally, in saline. The formulations can also comprise a polymer and a sugar and/or a polyalcohol excipient, preferably, in saline. The pH of the formulations is between 4 to 7, preferably, between 4.5 to 6.5, even more preferably between 5 to 6, and particularly, about 5.5. Such pH of the formulations advantageously provides solubility to the formulations and allows filter sterilization of the formulations.

In certain embodiments, the invention provides formulations comprising any of the polymers disclosed herein and cyclodextrin.

The cyclodextrin can be, for example, α-Cyclodextrin, β-Cyclodextrin, 2-Hydroxypropyl-β-cyclodextrin, Methylated β-cyclodextrin, Sulfobutylether β-cyclodextrin, or 2-Hydroxypropyl-γ-cyclodextrin. In further preferred embodiments, the cyclodextrin is 2-Hydroxypropyl-β-cyclodextrin. The concentration of cyclodextrin may be, for example, from 5% to 40%, 10% to 35%, or 15% to 25%.

The composition can be formed by, for example, combining a salt of the polymer with the cyclodextrin in an aqueous solution.

In a specific embodiment the formulation contains 20% (w/v) hydroxypropyl-β-cyclodextrin (HPBCD), approximately 0.01 N HCl and 6 mg/mL SEQ ID NO: 1 to 5, at a final pH 4.75-5.25.

In other embodiments, the polymer may be formulated with, for example, propylene glycol, chremophore, polyethylene glycol and/or polysorbate.

The formulation may be a suspension or a solution. In preferred embodiments, the formulation is a solution.

In addition to the polymers of the invention, the pharmaceutical compositions of the invention can further comprise lysophosphatidic acid (LPA) and/or an antidepressant, such as amitriptyline. Inclusion of these additional agents would facilitate treatment via inhibition of efflux pumps and enhancement of brain or intestinal uptake.

Another aspect of the invention is directed to the use of the compositions described herein in a method of treating a patient having a condition that responds to an agonist of μ-opioid receptor. Such a method comprises administering to the patient an effective amount of a pharmaceutical composition of the subject invention. In certain embodiments, a combination of any of the polymers disclosed herein and LPA and/or an antidepressant, such as amitriptyline, is administered to a subject.

The condition that can be treated according to the methods of the invention include: (i) analgesia (pain relief), (ii) a gastrointestinal disorder such as diarrhea, (iii) an opioid drug dependence, (iv) neuropathic pain, (v) schizophrenia, (vi) obesity, (vii) abnormal blood pressure, (viii) convulsions, ix) seizures, or (v) any condition for which an opioid is indicated.

In some embodiments, the pharmaceutical compositions of the subject invention can be used to treat acute or chronic pain. Uses for the compositions also include, but are not limited to, use as antimigraine agents, immunomodulatory agents, immunosuppressive agents and/or anti-arthritic agents.

Certain embodiments of the methods of the present invention, such as treatment of pain or opioid drug dependence, are directed to patients having a history of opioid substance abuse.

In certain embodiments of the present methods, the composition of the subject invention is administered parenterally. The administration may be done by, for example, intravenous, intramuscular, or subcutaneous administration. In other embodiments, the composition is administered orally.

The pharmaceutical compositions can be delivered in any suitable dosage form, such as, for example, a liquid, gel, solid, cream, or paste dosage form. In one embodiment, the compositions can be adapted to give sustained release of the polymer.

The pharmaceutical compositions include, but are not limited to, those forms suitable for oral, rectal, nasal, topical, (including buccal and sublingual), transdermal, vaginal, parenteral (including intramuscular, subcutaneous, and intravenous), spinal (epidural, intrathecal), and central (intracerebroventricular) administration. The compositions can, where appropriate, be conveniently provided in discrete dosage units.

Selected Definitions

As used herein, the singular forms "a", "an" and "the" are intended to include the plural forms as well, unless the context clearly indicates otherwise. Further, to the extent that the terms "including", "includes", "having", "has", "with", or variants thereof are used in either the detailed description and/or the claims, such terms are intended to be inclusive in a manner similar to the term "comprising."

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which will depend in part on how the value is measured or determined, i.e., the limitations of the measurement system. Where particular values are described in the application and claims, unless otherwise stated the term "about" meaning within an acceptable error range for the particular value should be assumed. In the context of compositions containing amounts of ingredients where the terms "about" or "approximately" are used, these compositions contain the stated amount of the ingredient with a variation (error range) of 0-10% around the value (X±10%).

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values.

When ranges are used herein, such as for dose ranges, combinations and subcombinations of ranges (e.g., subranges within the disclosed range), specific embodiments therein are intended to be explicitly included.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a polymer of the invention that is pharmaceutically acceptable and that possesses the desired pharmacological activity of the parent polymer. In particular, such salts are non-toxic may be inorganic or organic acid addition salts and base addition salts.

"Pharmaceutically acceptable vehicle" refers to a diluent, adjuvant, excipient or carrier with which a polymer of the invention is administered. A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

"Subject" includes humans or non-human animals, particularly, mammals, such as bovine, porcine, canine, rodent, or feline animals. The terms "patient" and "subject" are used interchangeably herein.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

As used herein, the terms "reducing," "inhibiting," "blocking," "preventing," alleviating," or "relieving" when referring to a polymer, mean that the polymer brings down the occurrence, severity, size, volume, or associated symptoms of a condition, event, or activity by at least about 7.5%, 10%, 12.5%, 15%, 17.5%, 20%, 22.5%, 25%, 27.5%, 30%, 35%, 40%, 45%, 50%, 55%, 60%, 65%, 70%, 75%, 80%, 90%, or 100% compared to how the condition, event, or activity would normally exist without application of the polymer or a composition comprising the polymer. The terms "increasing," "elevating," "enhancing," "upregulating," "improving," or "activating" when referring to a polymer mean that the polymer increases the occurrence or activity of a condition, event, or activity by at least about 7.5%, 10%, 12.5%, 15%, 17.5%, 20%, 22.5%, 25%, 27.5%, 30%, 35%, 40%, 45%, 50%, 55%, 60%, 65%, 70%, 75%, 80%, 90%, 100%, 150%, 200%, 250%, 300%, 400%, 500%, 750%, or 1000% compared to how the condition, event, or activity would normally exist without application of the polymer or a composition comprising the polymer.

In treatment methods according to the invention, a therapeutically effective amount of a pharmaceutical agent according to the invention is administered to a subject suffering from or diagnosed as having such a disease, disorder, or condition. A "therapeutically effective amount" means an amount or dose sufficient to generally bring about the desired therapeutic or prophylactic benefit in patients in need of such treatment for the designated disease, disorder, or condition.

Effective amounts or doses of the polymers of the present invention may be ascertained by routine methods such as modeling, dose escalation studies or clinical trials, and by taking into consideration routine factors, e.g., the mode or route of administration or drug delivery, the pharmacokinetics of the polymer, the severity and course of the disease, disorder, or condition, the subject's previous or ongoing therapy, the subject's health status and response to drugs, and the judgment of the treating physician. An example of a dose is in the range of from about 0.001 to about 200 mg of polymer per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

"Polymers," and equivalent expressions, refer to compounds having a molecular structure comprising chiefly or entirely of a number of residues bonded together. Polymers described herein include compounds having one or more residues of amino acids and/or organic acids. Accordingly, a "residue" includes an amino acid or an organic acid.

"Amino acid" as used herein refers to organic compounds containing amine and carboxyl functional groups, along with a side chain specific to each amino acid. Amino acids envisioned in the instant invention include natural or synthetic amino acids.

"Organic acid" as used herein refers to organic compounds with acidic properties. Organic acids include carboxylic acids, whose acidity is associated with their carboxyl group. Organic acids envisioned in the instant invention include natural or synthetic organic acids.

"Peptides," and equivalent expressions, refer to refer to compounds having a molecular structure comprising chiefly or entirely of a number of amino acids bonded together. Peptides of the invention can be conjugated to one or more moieties as disclosed herein.

Routes of Administration and Dosage Forms

In certain embodiments, the polymers may be administered intramuscularly, subcutaneously, intrathecally, intravenously or intraperitoneally by infusion or injection. Solutions of the polymers can be prepared in water, optionally mixed with a nontoxic surfactant. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the polymers that are adapted for the extemporaneous preparation of sterile injectable or infusible solutions or dispersions, optionally encapsulated in liposomes. Preferably, the ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained by, for example, the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by the use in the compositions of agents delaying absorption, for example, aluminum monostearate and gelatin.

Sterile injectable solutions are prepared by incorporating the polymers in the required amount in the appropriate solvent as described herein with various of the other ingredients enumerated herein, as required, preferably followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

The compositions of the subject invention may also be administered orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet.

For oral therapeutic administration, the polymers may be combined with one or more excipients and used in the form of ingestible tablets, buccal tablets, troches, capsules, elixirs, suspensions, syrups, wafers, and the like. Such compositions and preparations should contain at least 0.1% of a polymer of the present invention. The percentage of the polymers of the invention present in such compositions and preparations may, of course, be varied and may conveniently be between about 2% to about 60% of the weight of a given unit dosage form. The amount of the polymers in such therapeutically useful compositions is such that an effective dosage level will be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid, and the like; a lubricant such as magnesium stearate; and a sweetening agent such as sucrose, fructose, lactose, or aspartame, or a flavoring agent such as peppermint, oil of wintergreen, or cherry flavoring may be added.

When the unit dosage form is a capsule, it may contain, in addition to materials of the above type, a liquid carrier, such as a vegetable oil or a polyethylene glycol.

Various other materials may be present as coatings or for otherwise modifying the physical form of the solid unit dosage form. For instance, tablets, pills, or capsules may be coated with gelatin, wax, shellac, or sugar, and the like. A syrup or elixir may contain the active polymer, sucrose or fructose as a sweetening agent, methyl and propylparabens as preservatives, a dye, and flavoring such as cherry or orange flavor.

Of course, any material used in preparing any unit dosage form should be pharmaceutically acceptable and substantially non-toxic in the amounts employed.

In addition, the polymers may be incorporated into sustained-release preparations and devices. For example, the polymers may be incorporated into time release capsules, time release tablets, time release pills, and time release polymers or nanoparticles.

Pharmaceutical compositions for topical administration of the polymers to the epidermis (mucosal or cutaneous surfaces) can be formulated as ointments, creams, lotions, gels, or as a transdermal patch. Such transdermal patches can contain penetration enhancers such as linalool, carvacrol, thymol, citral, menthol, t-anethole, and the like. Ointments and creams can, for example, include an aqueous or oily base with the addition of suitable thickening agents, gelling agents, colorants, and the like. Lotions and creams can include an aqueous or oily base and typically also contain one or more emulsifying agents, stabilizing agents, dispersing agents, suspending agents, thickening agents, coloring agents, and the like. Gels preferably include an aqueous carrier base and include a gelling agent such as cross-linked polyacrylic acid polymer, a derivatized polysaccharide (e.g., carboxymethyl cellulose), and the like.

Pharmaceutical compositions suitable for topical administration in the mouth (e.g., buccal or sublingual administration) include lozenges comprising the composition in a flavored base, such as sucrose, acacia, or tragacanth; pastilles comprising the composition in an inert base such as gelatin and glycerin or sucrose and acacia; and mouthwashes comprising the active ingredient in a suitable liquid carrier. The pharmaceutical compositions for topical administration in the mouth can include penetration enhancing agents, if desired.

Useful solid carriers include finely divided solids such as talc, clay, microcrystalline cellulose, silica, alumina, and the like. Other solid carriers include nontoxic polymeric nanoparticles or microparticles. Useful liquid carriers include water, alcohols, or glycols, or water/alcohol/glycol blends, in which the polymers can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of useful dermatological compositions which can be used to deliver the polymers to the skin are known in the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), all of which are hereby incorporated by reference.

The concentration of the therapeutic polymers of the invention in such formulations can vary widely depending on the nature of the formulation and intended route of administration. For example, the concentration of the polymers in a liquid composition, such as a lotion, can preferably be from about 0.1-25% by weight, or, more preferably, from about 0.5-10% by weight. The concentration in a semi-solid or solid composition such as a gel or a powder can preferably be about 0.1-5% by weight, or, more preferably, about 0.5-2.5% by weight.

Pharmaceutical compositions for spinal administration or injection into amniotic fluid can be provided in unit dose form in ampoules, pre-filled syringes, small volume infusion, or in multi-dose containers, and can include an added preservative. The compositions for parenteral administration can be suspensions, solutions, or emulsions, and can contain excipients such as suspending agents, stabilizing agents, and dispersing agents.

A pharmaceutical composition suitable for rectal administration comprises a polymer of the present invention in combination with a solid or semisolid (e.g., cream or paste) carrier or vehicle. For example, such rectal compositions can be provided as unit dose suppositories. Suitable carriers or vehicles include cocoa butter and other materials commonly used in the art.

According to one embodiment, pharmaceutical compositions of the present invention suitable for vaginal administration are provided as pessaries, tampons, creams, gels, pastes, foams, or sprays containing a polymer of the invention in combination with carriers as are known in the art. Alternatively, compositions suitable for vaginal administration can be delivered in a liquid or solid dosage form.

Pharmaceutical compositions suitable for intra-nasal administration are also encompassed by the present invention. Such intra-nasal compositions comprise a polymer of the invention in a vehicle and suitable administration device to deliver a liquid spray, dispersible powder, or drops. Drops may be formulated with an aqueous or non-aqueous base also comprising one or more dispersing agents, solubilizing agents, or suspending agents. Liquid sprays are conveniently delivered from a pressurized pack, an insufflator, a nebulizer, or other convenient means of delivering an aerosol comprising the polymer. Pressurized packs comprise a suitable propellant such as dichlorodifluoromethane, trichlorofluoromethane, dichlorotetrafluoroethane, carbon dioxide, or other suitable gas as is well known in the art. Aerosol dosages can be controlled by providing a valve to deliver a metered amount of the polymer.

The polymers may be combined with an inert powdered carrier and inhaled by the subject or insufflated.

Pharmaceutical compositions for administration by inhalation or insufflation can be provided in the form of a dry powder composition, for example, a powder mix of the polymer and a suitable powder base such as lactose or starch. Such powder composition can be provided in unit dosage form, for example, in capsules, cartridges, gelatin packs, or blister packs, from which the powder can be administered with the aid of an inhalator or insufflator.

The exact amount (effective dose) of the agent will vary from subject to subject, depending on, for example, the species, age, weight, and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., The Pharmacological Basis of Therapeutics, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. Methods for the extrapolation of effective dosages in mice and other animals to humans are known to the art; for example, see U.S. Pat. No. 4,938,949, which is hereby incorporated by reference. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.001 to about 100 mg/kg of body weight per day, preferably from about 0.01 to about 100 mg/kg of body weight per day, more preferably, from about 0.1 to about 50 mg/kg of body weight per day, or even more preferred, in a range of from about 1 to about 10 mg/kg of body weight per day. For example, a suitable dose may be about 1 mg/kg, 10 mg/kg, or 50 mg/kg of body weight per day.

The polymers can be conveniently administered in unit dosage form, containing for example, about 0.05 to about 10000 mg, about 0.5 to about 10000 mg, about 5 to about 1000 mg, or about 50 to about 500 mg of active ingredient per unit dosage form.

The polymers can be administered to achieve peak plasma concentrations of, for example, from about 0.25 to about 200 µM, about 0.5 to about 75 µM, about 1 to about 50 µM, about 2 to about 30 or about 5 to about 25 µM. Exemplary desirable plasma concentrations include at least 0.25, 0.5, 1, 5, 10, 25, 50, 75, 100 or 200 µM. For example, plasma levels may be from about 1 to about 100 micromolar or from about 10 to about 25 micromolar. This may be achieved, for example, by the intravenous injection of a 0.05 to 5% solution of the polymers, optionally in saline, or orally administered as a bolus containing about 1 to about 100 mg of the polymers. Desirable blood levels may be maintained by continuous or intermittent infusion.

SEQ ID NO: 1 to 5 or other µ-opioid receptor binding polymers will be included in the compositions within a therapeutically useful and effective concentration range, as determined by routine methods that are well known in the medical and pharmaceutical arts. For example, a typical composition can include one or more of the polymer at a concentration in the range of at least about 1 mg/ml, preferably at least about 4 mg/ml, more preferably at least 5 mg/ml and most preferably at least 6 mg/ml.

The polymers may conveniently be presented in a single dose or as divided doses administered at appropriate intervals, for example, as one dose per day or as two, three, four or more sub-doses per day. The sub-dose itself may be further divided, e.g., into a number of discrete loosely spaced administrations; such as multiple inhalations from an insufflator.

Optionally, the pharmaceutical compositions of the present invention can include one or more other therapeutic agents, e.g., as a combination therapy. The additional therapeutic agent(s) will be included in the compositions within a therapeutically useful and effective concentration range, as determined by routine methods that are well known in the medical and pharmaceutical arts. The concentration of any particular additional therapeutic agent may be in the same range as is typical for use of that agent as a monotherapy, or the concentration may be lower than a typical monotherapy concentration if there is a synergy when combined with a polymer of the present invention.

Methods of Treatment

The present invention provides for the use of the compositions of the subject invention for treatment of conditions that can be improved through binding at the µ-opioid receptor. This can include, for example, pain, discomfort associated with gastrointestinal disorders, and treatment of drug dependence.

Methods for providing analgesia (alleviating or reducing pain), relief from gastrointestinal disorders such as diarrhea, and therapy for drug dependence in patients, such as mammals, including humans, comprise administering to a patient suffering from one of the aforementioned conditions an effective amount of the composition of the subject invention.

Diarrhea may be caused by a number of sources, such as infectious disease, cholera, or an effect or side-effect of various drugs or therapies, including those used for cancer therapy. Preferably, the polymer is administered parenterally or enterally. The dosage of the effective amount of the polymers can vary depending upon the age and condition of each individual patient to be treated. However, suitable unit dosages typically range from about 0.01 to about 100 mg. For example, a unit dose can be in the range of about 0.2 mg to about 50 mg. Such a unit dose can be administered more than once a day, e.g., two or three times a day.

All documents, references, and information, including, but not limited to, journal articles, patent applications, and patents, that are mentioned, cited, or referred to in this application are hereby incorporated by reference in their entirety.

We claim:

1. A polymer having a sequence SEQ ID NO: 1: $Tyr^1$-$Xaa^2$-$Xaa^3$-$Phe^4$ or a salt thereof, wherein $Xaa^2$ is D-serine, D-threonine, D-glutamate, D-aspartate, D-glutamine, D-asparagine, D-arginine, or D-histidine, and $Xaa^3$ is tryptophan, wherein said polymer is not conjugated, and wherein said polymer is linear and the C-terminus of $Phe^4$ is modified with —$NH_2$.

2. The polymer of claim 1, wherein $Xaa^2$ is D-serine.
3. The polymer of claim 1, wherein $Xaa^2$ is D-threonine.
4. The polymer of claim 1, wherein $Xaa^2$ is D-glutamate.
5. The polymer of claim 1, wherein $Xaa^2$ is D-aspartate.
6. The polymer of claim 1, wherein $Xaa^2$ is D-glutamine.
7. The polymer of claim 1, wherein $Xaa^2$ is D-asparagine.
8. The polymer of claim 1, wherein $Xaa^2$ is D-arginine.
9. The polymer of claim 1, wherein $Xaa^2$ is D-histidine.

10. A polymer having a sequence SEQ ID NO: 1: $Tyr^1$-$Xaa^2$-$Xaa^3$-$Phe^4$ or a salt thereof, wherein $Xaa^2$ is D-lysine, $Xaa^3$ is tryptophan, and wherein said polymer is linear, and said polymer is not conjugated, except the C-terminus of $Phe^4$ is optionally modified with —$NH_2$.

11. A composition comprising one or more of the polymer according to claim 10 and a pharmaceutically acceptable carrier and/or excipient.

12. The composition of claim 11, wherein the pharmaceutically acceptable carrier and/or excipient comprises one or more of saline, cyclodextrin, polyethylene glycol, a sugar, and a poly-alcohol; and optionally, further comprises lysophosphatidic acid (LPA) and/or amitriptyline.

13. The composition of claim 11, having a pH of 4 to 7.

* * * * *

UNITED STATES PATENT AND TRADEMARK OFFICE
CERTIFICATE OF CORRECTION

| | | |
|---|---|---|
| PATENT NO. | : 12,146,002 B2 | Page 1 of 1 |
| APPLICATION NO. | : 17/724913 | |
| DATED | : November 19, 2024 | |
| INVENTOR(S) | : Theodore E. Maione, James Hamsher and Constantine Basil Maglaris | |

It is certified that error appears in the above-identified patent and that said Letters Patent is hereby corrected as shown below:

In the Specification

Column 6:
Line 26, "selected from N112, an" should read -- selected from $NH_2$, an --

Column 10:
Line 41, "hydroxypropyl-β-cyclodextrin (HPBCD)," should read -- hydroxypropyl-β-cyclodextrin (HPßCD), --

Column 17:
Line 24, "about 2 to about 30 or about 5" should read -- about 2 to about 30 μM, or about 5 --

Signed and Sealed this
Tenth Day of June, 2025

Coke Morgan Stewart
*Acting Director of the United States Patent and Trademark Office*

SEQUENCE LISTING

```
<160> NUMBER OF SEQ ID NOS: 36

<210> SEQ ID NO 1
<211> LENGTH: 4
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa can be any amino acid; a residue other than
      lysine, glutamate, aspartate, ornithine, or proline; or a residue
      as disclosed in the specification
<220> FEATURE:
<221> NAME/KEY: MISC_FEATURE
<222> LOCATION: (3)..(3)
<223> OTHER INFORMATION: Xaa can be any amino acid or a residue other
      than an aromatic amino acid

<400> SEQUENCE: 1
```

Tyr Xaa Xaa Phe
1

<210> SEQ ID NO 2
<211> LENGTH: 5
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa can be any amino acid; a residue other than
      lysine, glutamate, aspartate, ornithine, or proline; or a residue
      as disclosed in the specification
<220> FEATURE:
<221> NAME/KEY: MISC_FEATURE
<222> LOCATION: (3)..(3)
<223> OTHER INFORMATION: Xaa can be any amino acid or a residue other
      than an aromatic amino acid

<400> SEQUENCE: 2

Tyr Xaa Xaa Phe Glu
1               5

<210> SEQ ID NO 3
<211> LENGTH: 5
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa can be any amino acid; a residue other than
      lysine, glutamate, aspartate, ornithine, or proline; or a residue
      as disclosed in the specification
<220> FEATURE:
<221> NAME/KEY: MISC_FEATURE
<222> LOCATION: (3)..(3)
<223> OTHER INFORMATION: Xaa can be any amino acid or a residue other
      than an aromatic amino acid

<400> SEQUENCE: 3

Tyr Xaa Xaa Phe Asp
1               5

<210> SEQ ID NO 4
<211> LENGTH: 5
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa can be any amino acid; a residue other than
      lysine, glutamate, aspartate, ornithine, or proline; or a residue
      as disclosed in the specification
<220> FEATURE:
<221> NAME/KEY: MISC_FEATURE
<222> LOCATION: (2)..(5)
<223> OTHER INFORMATION: Residues 2 and 5 form a cyclic structure
<220> FEATURE:
<221> NAME/KEY: MISC_FEATURE
<222> LOCATION: (3)..(3)
<223> OTHER INFORMATION: Xaa can be any amino acid or a residue other
      than an aromatic amino acid

<400> SEQUENCE: 4

Tyr Xaa Xaa Phe Glu
1               5

```
<210> SEQ ID NO 5
<211> LENGTH: 5
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa can be any amino acid; a residue other than
      lysine, glutamate, aspartate, ornithine, or proline; or a residue
      as disclosed in the specification
<220> FEATURE:
<221> NAME/KEY: MISC_FEATURE
<222> LOCATION: (2)..(5)
<223> OTHER INFORMATION: Residues 2 and 5 form a cyclic structure
<220> FEATURE:
<221> NAME/KEY: MISC_FEATURE
<222> LOCATION: (3)..(3)
<223> OTHER INFORMATION: Xaa can be any amino acid or a residue other
      than an aromatic amino acid

<400> SEQUENCE: 5

Tyr Xaa Xaa Phe Asp
1               5

<210> SEQ ID NO 6
<211> LENGTH: 4
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa is D-lysine, D-serine, D-threonine,
      D-glutamate, D-aspartate, D-glutamine, D-asparagine, D-arginine,
      D-histidine, L-4-oxaproline, D-4-oxaproline, L-4-thioproline,
      D-4-thioproline, L-2-azaproline, D-2-azaproline,
      L-4-hydroxyproline, D-4-hydroxyproline, 1,5-disubstituted
      tetrazole, 2-amino isobutyric acid, sarcosine,
      1-aminocyclopentane-1-carboxylic acid, beta-alanine,
      2-amino-cyclopentane carboxylic acid (beta-proline),
      D-5-hydroxylysine, D-hydroxylysine-5-sulfate, D-hydroxylysine-5-
      nitrate, D-hydroxylysine-5-phosphate, D-serine-3-sulfate,
      D-threonine-3-sulfate, D-serine-3-nitrate, D-threonine-3-nitrate,
      D-serine-3-phosphate, or D-threonine-3-phosphate
<220> FEATURE:
<221> NAME/KEY: MISC_FEATURE
<222> LOCATION: (2)..(4)
<223> OTHER INFORMATION: Residues 2 and 4 can form a cyclic structure,
      except when Xaa is D-lysine, the polymer is linear
<220> FEATURE:
<221> NAME/KEY: MISC_FEATURE
<222> LOCATION: (3)..(3)
<223> OTHER INFORMATION: Xaa is tryptophan
<220> FEATURE:
<221> NAME/KEY: MISC_FEATURE
<222> LOCATION: (4)..(4)
<223> OTHER INFORMATION: Phe can be modified by conjugation to -NH2

<400> SEQUENCE: 6

Tyr Xaa Xaa Phe
1

<210> SEQ ID NO 7

<400> SEQUENCE: 7

000

<210> SEQ ID NO 8
```

```
<211> LENGTH: 4
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa is D-lysine
<220> FEATURE:
<221> NAME/KEY: MISC_FEATURE
<222> LOCATION: (3)..(3)
<223> OTHER INFORMATION: Xaa is tryptophan
<220> FEATURE:
<221> NAME/KEY: MISC_FEATURE
<222> LOCATION: (4)..(4)
<223> OTHER INFORMATION: Phe can be modified by conjugation to -NH2

<400> SEQUENCE: 8

Tyr Xaa Xaa Phe
1

<210> SEQ ID NO 9
<211> LENGTH: 4
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa is D-serine
<220> FEATURE:
<221> NAME/KEY: MISC_FEATURE
<222> LOCATION: (3)..(3)
<223> OTHER INFORMATION: Xaa is tryptophan
<220> FEATURE:
<221> NAME/KEY: MISC_FEATURE
<222> LOCATION: (4)..(4)
<223> OTHER INFORMATION: Phe can be modified by conjugation to -NH2

<400> SEQUENCE: 9

Tyr Xaa Xaa Phe
1

<210> SEQ ID NO 10
<211> LENGTH: 4
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa is D-threonine
<220> FEATURE:
<221> NAME/KEY: MISC_FEATURE
<222> LOCATION: (3)..(3)
<223> OTHER INFORMATION: Xaa is tryptophan
<220> FEATURE:
<221> NAME/KEY: MISC_FEATURE
<222> LOCATION: (4)..(4)
<223> OTHER INFORMATION: Phe can be modified by conjugation to -NH2

<400> SEQUENCE: 10

Tyr Xaa Xaa Phe
1

<210> SEQ ID NO 11
<211> LENGTH: 4
<212> TYPE: PRT
<213> ORGANISM: Artificial sequence
<220> FEATURE:
```

```
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa is D-glutamate
<220> FEATURE:
<221> NAME/KEY: MISC_FEATURE
<222> LOCATION: (3)..(3)
<223> OTHER INFORMATION: Xaa is tryptophan
<220> FEATURE:
<221> NAME/KEY: MISC_FEATURE
<222> LOCATION: (4)..(4)
<223> OTHER INFORMATION: Phe can be modified by conjugation to -NH2

<400> SEQUENCE: 11

Tyr Xaa Xaa Phe
1

<210> SEQ ID NO 12
<211> LENGTH: 4
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa is D-aspartate
<220> FEATURE:
<221> NAME/KEY: MISC_FEATURE
<222> LOCATION: (3)..(3)
<223> OTHER INFORMATION: Xaa is tryptophan
<220> FEATURE:
<221> NAME/KEY: MISC_FEATURE
<222> LOCATION: (4)..(4)
<223> OTHER INFORMATION: Phe can be modified by conjugation to -NH2

<400> SEQUENCE: 12

Tyr Xaa Xaa Phe
1

<210> SEQ ID NO 13
<211> LENGTH: 4
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa is D-glutamine
<220> FEATURE:
<221> NAME/KEY: MISC_FEATURE
<222> LOCATION: (3)..(3)
<223> OTHER INFORMATION: Xaa is tryptophan
<220> FEATURE:
<221> NAME/KEY: MISC_FEATURE
<222> LOCATION: (4)..(4)
<223> OTHER INFORMATION: Phe can be modified by conjugation to -NH2

<400> SEQUENCE: 13

Tyr Xaa Xaa Phe
1

<210> SEQ ID NO 14
<211> LENGTH: 4
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
```

```
<223> OTHER INFORMATION: Xaa is D-asparagine
<220> FEATURE:
<221> NAME/KEY: MISC_FEATURE
<222> LOCATION: (3)..(3)
<223> OTHER INFORMATION: Xaa is tryptophan
<220> FEATURE:
<221> NAME/KEY: MISC_FEATURE
<222> LOCATION: (4)..(4)
<223> OTHER INFORMATION: Phe can be modified by conjugation to -NH2

<400> SEQUENCE: 14

Tyr Xaa Xaa Phe
1

<210> SEQ ID NO 15
<211> LENGTH: 4
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa is D-arginine
<220> FEATURE:
<221> NAME/KEY: MISC_FEATURE
<222> LOCATION: (3)..(3)
<223> OTHER INFORMATION: Xaa is tryptophan
<220> FEATURE:
<221> NAME/KEY: MISC_FEATURE
<222> LOCATION: (4)..(4)
<223> OTHER INFORMATION: Phe can be modified by conjugation to -NH2

<400> SEQUENCE: 15

Tyr Xaa Xaa Phe
1

<210> SEQ ID NO 16
<211> LENGTH: 4
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa is D-histidine
<220> FEATURE:
<221> NAME/KEY: MISC_FEATURE
<222> LOCATION: (3)..(3)
<223> OTHER INFORMATION: Xaa is tryptophan
<220> FEATURE:
<221> NAME/KEY: MISC_FEATURE
<222> LOCATION: (4)..(4)
<223> OTHER INFORMATION: Phe can be modified by conjugation to -NH2

<400> SEQUENCE: 16

Tyr Xaa Xaa Phe
1

<210> SEQ ID NO 17
<211> LENGTH: 4
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa is L-4-oxaproline or D-4-oxaproline
<220> FEATURE:
<221> NAME/KEY: MISC_FEATURE
<222> LOCATION: (3)..(3)
```

```
<223> OTHER INFORMATION: Xaa is tryptophan
<220> FEATURE:
<221> NAME/KEY: MISC_FEATURE
<222> LOCATION: (4)..(4)
<223> OTHER INFORMATION: Phe can be modified by conjugation to -NH2

<400> SEQUENCE: 17

Tyr Xaa Xaa Phe
1

<210> SEQ ID NO 18
<211> LENGTH: 4
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa is L-4-thioproline or D-4-thioproline
<220> FEATURE:
<221> NAME/KEY: MISC_FEATURE
<222> LOCATION: (3)..(3)
<223> OTHER INFORMATION: Xaa is tryptophan
<220> FEATURE:
<221> NAME/KEY: MISC_FEATURE
<222> LOCATION: (4)..(4)
<223> OTHER INFORMATION: Phe can be modified by conjugation to -NH2

<400> SEQUENCE: 18

Tyr Xaa Xaa Phe
1

<210> SEQ ID NO 19
<211> LENGTH: 4
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa is L-2-azaproline or D-2-azaproline
<220> FEATURE:
<221> NAME/KEY: MISC_FEATURE
<222> LOCATION: (3)..(3)
<223> OTHER INFORMATION: Xaa is tryptophan
<220> FEATURE:
<221> NAME/KEY: MISC_FEATURE
<222> LOCATION: (4)..(4)
<223> OTHER INFORMATION: Phe can be modified by conjugation to -NH2

<400> SEQUENCE: 19

Tyr Xaa Xaa Phe
1

<210> SEQ ID NO 20
<211> LENGTH: 4
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa is D-4-hydroxyproline or L-4-hydroxyproline
<220> FEATURE:
<221> NAME/KEY: MISC_FEATURE
<222> LOCATION: (3)..(3)
<223> OTHER INFORMATION: Xaa is tryptophan
<220> FEATURE:
<221> NAME/KEY: MISC_FEATURE
<222> LOCATION: (4)..(4)
```

<223> OTHER INFORMATION: Phe can be modified by conjugation to -NH2

<400> SEQUENCE: 20

Tyr Xaa Xaa Phe
1

<210> SEQ ID NO 21
<211> LENGTH: 4
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa is 1,5-disubstituted tetrazole
<220> FEATURE:
<221> NAME/KEY: MISC_FEATURE
<222> LOCATION: (3)..(3)
<223> OTHER INFORMATION: Xaa is tryptophan
<220> FEATURE:
<221> NAME/KEY: MISC_FEATURE
<222> LOCATION: (4)..(4)
<223> OTHER INFORMATION: Phe can be modified by conjugation to -NH2

<400> SEQUENCE: 21

Tyr Xaa Xaa Phe
1

<210> SEQ ID NO 22
<211> LENGTH: 4
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa is 2-amino isobutyric acid
<220> FEATURE:
<221> NAME/KEY: MISC_FEATURE
<222> LOCATION: (3)..(3)
<223> OTHER INFORMATION: Xaa is tryptophan
<220> FEATURE:
<221> NAME/KEY: MISC_FEATURE
<222> LOCATION: (4)..(4)
<223> OTHER INFORMATION: Phe can be modified by conjugation to -NH2

<400> SEQUENCE: 22

Tyr Xaa Xaa Phe
1

<210> SEQ ID NO 23
<211> LENGTH: 4
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa is sarcosine
<220> FEATURE:
<221> NAME/KEY: MISC_FEATURE
<222> LOCATION: (3)..(3)
<223> OTHER INFORMATION: Xaa is tryptophan
<220> FEATURE:
<221> NAME/KEY: MISC_FEATURE
<222> LOCATION: (4)..(4)
<223> OTHER INFORMATION: Phe can be modified by conjugation to -NH2

<400> SEQUENCE: 23

Tyr Xaa Xaa Phe
1

<210> SEQ ID NO 24
<211> LENGTH: 4
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa is 1-aminocyclopentane-1-carboxylic acid
<220> FEATURE:
<221> NAME/KEY: MISC_FEATURE
<222> LOCATION: (3)..(3)
<223> OTHER INFORMATION: Xaa is tryptophan
<220> FEATURE:
<221> NAME/KEY: MISC_FEATURE
<222> LOCATION: (4)..(4)
<223> OTHER INFORMATION: Phe can be modified by conjugation to -NH2

<400> SEQUENCE: 24

Tyr Xaa Xaa Phe
1

<210> SEQ ID NO 25
<211> LENGTH: 4
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa is beta-alanine
<220> FEATURE:
<221> NAME/KEY: MISC_FEATURE
<222> LOCATION: (3)..(3)
<223> OTHER INFORMATION: Xaa is tryptophan
<220> FEATURE:
<221> NAME/KEY: MISC_FEATURE
<222> LOCATION: (4)..(4)
<223> OTHER INFORMATION: Phe can be modified by conjugation to -NH2

<400> SEQUENCE: 25

Tyr Xaa Xaa Phe
1

<210> SEQ ID NO 26
<211> LENGTH: 4
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa is 2-amino-cyclopentane carboxylic acid
      (beta-proline)
<220> FEATURE:
<221> NAME/KEY: MISC_FEATURE
<222> LOCATION: (3)..(3)
<223> OTHER INFORMATION: Xaa is tryptophan
<220> FEATURE:
<221> NAME/KEY: MISC_FEATURE
<222> LOCATION: (4)..(4)
<223> OTHER INFORMATION: Phe can be modified by conjugation to -NH2

<400> SEQUENCE: 26

Tyr Xaa Xaa Phe
1

```
<210> SEQ ID NO 27
<211> LENGTH: 4
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa is D-5-hydroxylysine
<220> FEATURE:
<221> NAME/KEY: MISC_FEATURE
<222> LOCATION: (2)..(4)
<223> OTHER INFORMATION: Residues 2 and 4 can form a cyclic structure
<220> FEATURE:
<221> NAME/KEY: MISC_FEATURE
<222> LOCATION: (3)..(3)
<223> OTHER INFORMATION: Xaa is tryptophan
<220> FEATURE:
<221> NAME/KEY: MISC_FEATURE
<222> LOCATION: (4)..(4)
<223> OTHER INFORMATION: Phe can be modified by conjugation to -NH2

<400> SEQUENCE: 27

Tyr Xaa Xaa Phe
1

<210> SEQ ID NO 28
<211> LENGTH: 4
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa is D-hydroxylysine-5-sulfate
<220> FEATURE:
<221> NAME/KEY: MISC_FEATURE
<222> LOCATION: (2)..(4)
<223> OTHER INFORMATION: Residues 2 and 4 form a cyclic structure
<220> FEATURE:
<221> NAME/KEY: MISC_FEATURE
<222> LOCATION: (3)..(3)
<223> OTHER INFORMATION: Xaa is tryptophan

<400> SEQUENCE: 28

Tyr Xaa Xaa Phe
1

<210> SEQ ID NO 29
<211> LENGTH: 4
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa is D-hydroxylysine-5-nitrate
<220> FEATURE:
<221> NAME/KEY: MISC_FEATURE
<222> LOCATION: (2)..(4)
<223> OTHER INFORMATION: Residues 2 and 4 form a cyclic structure
<220> FEATURE:
<221> NAME/KEY: MISC_FEATURE
<222> LOCATION: (3)..(3)
<223> OTHER INFORMATION: Xaa is tryptophan

<400> SEQUENCE: 29

Tyr Xaa Xaa Phe
1
```

```
<210> SEQ ID NO 30
<211> LENGTH: 4
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa is D-hydroxylysine-5-phosphate
<220> FEATURE:
<221> NAME/KEY: MISC_FEATURE
<222> LOCATION: (2)..(4)
<223> OTHER INFORMATION: Residues 2 and 4 form a cyclic structure
<220> FEATURE:
<221> NAME/KEY: MISC_FEATURE
<222> LOCATION: (3)..(3)
<223> OTHER INFORMATION: Xaa is tryptophan

<400> SEQUENCE: 30

Tyr Xaa Xaa Phe
1

<210> SEQ ID NO 31
<211> LENGTH: 4
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa is D-serine-3-sulfate
<220> FEATURE:
<221> NAME/KEY: MISC_FEATURE
<222> LOCATION: (3)..(3)
<223> OTHER INFORMATION: Xaa is tryptophan
<220> FEATURE:
<221> NAME/KEY: MISC_FEATURE
<222> LOCATION: (4)..(4)
<223> OTHER INFORMATION: Phe can be modified by conjugation to -NH2

<400> SEQUENCE: 31

Tyr Xaa Xaa Phe
1

<210> SEQ ID NO 32
<211> LENGTH: 4
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa is D-threonine-3-sulfate
<220> FEATURE:
<221> NAME/KEY: MISC_FEATURE
<222> LOCATION: (3)..(3)
<223> OTHER INFORMATION: Xaa is tryptophan
<220> FEATURE:
<221> NAME/KEY: MISC_FEATURE
<222> LOCATION: (4)..(4)
<223> OTHER INFORMATION: Phe can be modified by conjugation to -NH2

<400> SEQUENCE: 32

Tyr Xaa Xaa Phe
1

<210> SEQ ID NO 33
<211> LENGTH: 4
<212> TYPE: PRT
```

```
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa is D-serine-3-nitrate
<220> FEATURE:
<221> NAME/KEY: MISC_FEATURE
<222> LOCATION: (3)..(3)
<223> OTHER INFORMATION: Xaa is tryptophan
<220> FEATURE:
<221> NAME/KEY: MISC_FEATURE
<222> LOCATION: (4)..(4)
<223> OTHER INFORMATION: Phe can be modified by conjugation to -NH2

<400> SEQUENCE: 33

Tyr Xaa Xaa Phe
1

<210> SEQ ID NO 34
<211> LENGTH: 4
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa is D-threonine-3-nitrate
<220> FEATURE:
<221> NAME/KEY: MISC_FEATURE
<222> LOCATION: (3)..(3)
<223> OTHER INFORMATION: Xaa is tryptophan
<220> FEATURE:
<221> NAME/KEY: MISC_FEATURE
<222> LOCATION: (4)..(4)
<223> OTHER INFORMATION: Phe can be modified by conjugation to -NH2

<400> SEQUENCE: 34

Tyr Xaa Xaa Phe
1

<210> SEQ ID NO 35
<211> LENGTH: 4
<212> TYPE: PRT
<213> ORGANISM: Artificial sequence
<220> FEATURE:
<223> OTHER INFORMATION: polymer agonist of Mu opioid receptors
<220> FEATURE:
<221> NAME/KEY: MISC_FEATURE
<222> LOCATION: (2)..(2)
<223> OTHER INFORMATION: Xaa is D-serine-3-phosphate
<220> FEATURE:
<221> NAME/KEY: MISC_FEATURE
<222> LOCATION: (3)..(3)
<223> OTHER INFORMATION: Xaa is tryptophan
<220> FEATURE:
<221> NAME/KEY: MISC_FEATURE
<222> LOCATION: (4)..(4)
<223> OTHER INFORMATION: Phe can be modified by conjugation to -NH2

<400> SEQUENCE: 35

Tyr Xaa Xaa Phe
1

<210> SEQ ID NO 36
<211> LENGTH: 4
<212> TYPE: PRT
<213> ORGANISM: Artificial sequence
<220> FEATURE:
<223> OTHER INFORMATION: polymer agonist of Mu opioid receptors
<220> FEATURE:
```

```
<221> NAME/KEY: MISC_FEATURE
<222> LOCATION: (2)..(2)
<223> OTHER INFORMATION: Xaa is D-threonine-3-phosphate
<220> FEATURE:
<221> NAME/KEY: MISC_FEATURE
<222> LOCATION: (3)..(3)
<223> OTHER INFORMATION: Xaa is tryptophan
<220> FEATURE:
<221> NAME/KEY: MISC_FEATURE
<222> LOCATION: (4)..(4)
<223> OTHER INFORMATION: Phe can be modified by conjugation to -NH2

<400> SEQUENCE: 36

Tyr Xaa Xaa Phe
1
```